United States Patent [19]

Doyle et al.

[11] Patent Number: 4,551,543

[45] Date of Patent: Nov. 5, 1985

[54] BIMETALLIC CARBONYL HYDROFORMYLATION CATALYSTS

[75] Inventors: Gerald Doyle, Whitehouse Station; Kenneth A. Eriksen, Phillipsburg, both of N.J.; Roy L. Pruett, Baton Rouge, La.

[73] Assignee: Exxon Research and Engineering Co., Florham Park, N.J.

[21] Appl. No.: 563,971

[22] Filed: Dec. 21, 1983

[51] Int. Cl.$^4$ .......................... C07F 1/08; C07F 15/00; C07F 15/06

[52] U.S. Cl. ........................................ 556/14; 556/31; 568/454; 502/161; 502/165; 502/166

[58] Field of Search ........................ 260/429 R, 438.1; 502/161

[56] References Cited

U.S. PATENT DOCUMENTS 3,998,864 12/1976 Trevillyan ...................... 260/429 R
4,288,380 9/1981 Billig et al. ..................... 260/429 R
4,301,086 11/1981 Pruett et al. ................ 260/429 R X
4,302,400 11/1981 McVicker ...................... 260/429 R
4,321,211 3/1982 McVicker ...................... 260/429 R Primary Examiner—Helen M. S. Sneed
Attorney, Agent, or Firm—Jay Simon; E. Thomas Wheelock

[57] ABSTRACT

A hydroformylation catalyst of the formula $$L_a CuCo(CO)_b L'_c$$

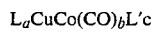

wherein L is a monodentate phosphine, a bidentate phosphine or a bidentate amine, a is 1-3, b is 3 or 4, c is 0 or 1; provided that, where b=4, c=0 and L' is CO, phosphine or phosphite. Where the catalysts have the formula $$L_a CuCo(CO)_4$$

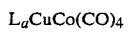

the compounds are novel.

28 Claims, No Drawings

BIMETALLIC CARBONYL HYDROFORMYLATION CATALYSTS

BACKGROUND OF THE INVENTION AND PRIOR ART

One of the oldest homogeneous catalytic reactions of olefins is hydroformylation, the addition of CO and hydrogen to produce aldehydes. The reaction is carried out commercially utilizing a suitable catalyst, e.g., cobalt catalyst, and may be illustrated as follows:

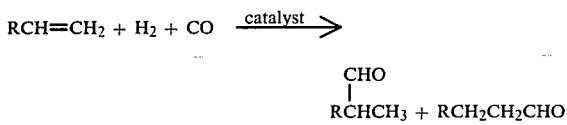

Alcohols may incidentally be formed as a result of hydrogenation.

The cobalt catalysts which have been used in hydroformylation reactions include $HCo(CO)_4$ and $Co_2(CO)_8$. However, these carbonyls are relatively unstable and volatile. Hence, they are difficult to separate from the reaction products for the recycling of catalyst. Additionally, these compounds have limited selectivity for the desired linear aldehydes and alcohols. Furthermore, these catalysts require high pressures, e.g., 200 atmospheres, at temperatures of about 120°–140° C. These severe reaction conditions impose economic penalties for high-pressure reactor investment and for construction and operation of the gas compressor. These problems have resulted in the development of phosphine modified cobalt catalysts and rhodium catalysts to give higher yields of linear aldehydes under mild conditions.

The phosphine modified cobalt catalysts are typified by the component $HCo(CO)_3(PBu_3)$. While this tributyl phosphine catalyst is more stable and may be used at lower pressures, e.g., 100 atmospheres, it is less active for hydroformylation than $HCo(CO)_4$ and yields an inferior rate even at elevated temperatures, e.g., 180° C. It is, however, much more active as a hydrogenation catalyst. As a result it has the further limitation that some olefin is lost through hydrogenation to alkane.

Rhodium analogs, e.g., $HRh(CO)(PPh_3)_3$, of the phosphine modified cobalt carbonyls have been prepared and utilized successfully as hydroformylation catalysts. While this compound is more stable than $HCo(CO)_4$ it requires excess phosphine ligand to stabilize it during product distillation and catalyst recycle. It is, however, advantageously selective toward the formation of a higher yield of the more desirable linear aldehydes. Despite its advantages (high selectivity and low-pressure operation), the high cost of rhodium inventory and recycle has limited its use.

There is a need for a low cost, stable, hydroformylation catalyst which has high selectivity and results in good yields at low pressures, e.g., 100 atmospheres or less. Although a large number of metal carbonyl compounds have been prepared, none other than the cobalt and rhodium compounds discussed above have been disclosed as being effective hydroformylation catalysts. Illustrative of the known metal carbonyl compounds are those disclosed in the prior art discussed below.

U.S. Pat. No. 3,824,221 discloses metallated polymers and copolymers where the polymer may be styryl phosphine and the metal is selected from Groups IVA to VIII and IB of the Periodic Table of the Elements. The metallated polymers are said to be hydroformylation catalysts.

Similarly, U.S. Pat. No. 4,111,856 discloses resin-metal compound complexes useful as hydroformylation catalysts. The metal can be transition metals including nickel, cobalt and rhodium. Copper is also disclosed as a suitable metal. These resin-metal compounds may contain one or more functional groups such as amine, carbonyl or phosphine. Neither U.S. Pat. No. 3,824,221 or 4,111,856 disclose bimetallic compounds containing copper.

U.S. Pat. No. 3,959,385 discloses hydroformylation catalysts comprising carbonyl complexes of metals in Group VIII of the Periodic Table of the Elements, the complexes being modified by trisubstituted organic phosphines which contain at least one carbonyl group.

Other metal carbonyl complexes useful as hydroformylation catalysts are disclosed in U.S. Pat. Nos. 4,259,530; 4,292,126 and 4,334,042. The metals suitable for use in the catalysts include cobalt and rhodium.

Certain bimetallic carbonyl complexes containing phosphines or amines are taught in the literature. For example, the CA Registry discloses a compound of the formula

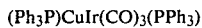

designated as CAS Registry No. 81506-93-6. Other bimetallic complexes which contain copper are disclosed in an article by Kuyper et al., "Metal-Metal Bonded Triazenido Compounds", J. Organomet. Chem. (1975), 96(2), 289–99. The compounds disclosed include:

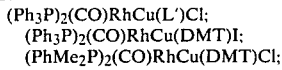

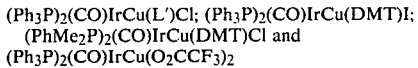

where L′=dimethyl triazene (DMT); methyl (p-tolyl) triazene ($M_p$TT) and di(p-tolyl) formanidine ($D_P$TF). Compounds of the structure

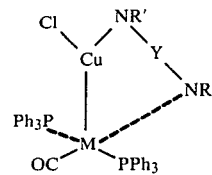

wherein M, Y, R and R′ are:
Rh, N $CH_3$, $CH_3$; respectively or
Ir, N, $CH_3$, $CH_3$ and phosphines are $PPhMe_2$;
Ir, N, $CH_3$, tolyl
Ir, CH, tolyl, Et.
are disclosed by Van Vleet et al in J. Organomet. Chem (1979), 182(1), 105–15. The aforedisclosed compounds of Kuyper et al have similar structures.

Related copper-cobalt complexes include $(Ph_3P)_3CuCo(CO)_3(PBu_3)$ and $(Triars)CuCo(CO)_4$ where Triars is $[(CH_3)_2AsCH_2]_3CCH_3$. None of these copper compounds have been said to exhibit catalytic activity in hydroformylation reactions. See for Example "Metal-Metal Bonds v. Complexes Containing Copper-Silver-Metal Linkages," A. S. Kasenally et al, J. Chem.

Soc., 1965 (Oct.) 5331-6 and "Synthesis of Transition Metal Derivatives of Magnesium," G. B. McVicker & R. S. Matyas, J. Chem. Soc., Chem. Commun., 1972, (17) 972.

The art discloses certain copper-cobalt carbonyl complexes of the formula "bipyCuCo(CO)$_4$]$_n$ where "bipy" is bipyridyl. See "Preparation, Structure and Reactions of New Complexes Containing Copper or Silver Bonded to Transition Metals", P. Hacket and; A. R. Manning, J. Chem. Soc., Dalton Trans. 1975(15) 1606-9. While this compound is taught to be a polymer it is these inventors belief that the compound is in fact bipyCuCo(CO)$_4$.

SUMMARY OF INVENTION

It has been surprisingly found that compounds having the general formula $$L_a CuM(CO)_b L'_c$$

where M is cobalt or rhodium, a is 1-3; b is 3 or 4 and c is 0 or 1; provided that when b=4, c=0, exhibit catalytic activity in hydroformylation reactions. In the above formula L is monodentate phosphine or a bidentate phosphine or amine compound of the formula R$_1$R$_2$Q(CH$_2$)$_n$QR$_3$R$_4$ where R$_1$, R$_2$, R$_3$ and R$_4$ may be the same or different and are each independently selected from the group consisting of alkyl, cycloalkyl and aryl, n is 1-4, Q is N or P, and L' is phosphine or phosphite. Preferably M is cobalt.

When b=4 the compound has the formula $$L_a CuM(CO)_4$$

These compounds are novel compounds.

DETAILED DESCRIPTION

This invention relates to copper-cobalt carbonyl complex useful as catalysts in hydroformylation reactions. More particularly it relates to monodentate phosphine and bidentate phosphine or amine complexes of the copper-cobalt carbonyls.

The compounds suitable for use as hydroformylation catalyst which are within the scope of this invention have the general formula $$L_a CuM(CO)_b L'_c$$

where M is cobalt or rhodium, L is a monodentate phosphine, a bidentate phosphine or a bidentate amine; L' is CO, phosphine or phosphite; a is 1-3, b is 3 or 4 and c is 0 or 1; provided that where b=4, c=0. Preferably M is cobalt. The bidentate phosphines and amines have the formuula:

$$R_1 R_2 Q(CH_2)_n QR_3 R_4$$

wherein R$_1$, R$_2$, R$_3$, and R$_4$ are the same or different and are independently selected from the group consisting of alkyl, cyclo alkyl, aryl, alkaryl and aralkyl; Q is N or P and n is 1-4.

Where the R groups are alkyl they can be C$_1$-C$_8$ alkyl, preferably C$_1$-C$_5$ alkyl. Illustrative examples of the C$_1$-C$_8$ alkyl radicals are methyl, ethyl, propyl, isopopyl, butyl, isobutyl, pentyl, isopentyl, hexyl, heptyl, octyl, etc. Where the R groups are cycloalkyl the cycloalkyl radicals can be C$_5$-C$_8$ cycloalkyl. Illustrative example of these cycloalkyl radicals are cyclopentyl, cyclohexyl, methylcyclohexyl, cyclooctyl. Where the R groups are derived from aromatic moieties, R may be C$_6$-C$_8$ aromatic radicals. Illustrative of these C$_6$-C$_8$ aromatic compounds are phenyl, benzyl, tolyl, xylyl, etc.

The monodentate phosphines of this invention have the formula R$_1$R$_2$R$_3$P wherein R$_1$, R$_2$ and R$_3$ are as previously defined. Preferably, R$_1$, R$_2$ and R$_3$ are methyl or phenyl.

The phosphites of this invention have the formula (R$_1$O)(R$_2$O)(R$_3$O)P wherein R$_1$, R$_2$, and R$_3$ are as previously defined. Preferably R$_1$, R$_2$ and R$_3$ are methyl, ethyl, or phenyl.

The preferred catalysts of this invention have the formula L$_a$CuM(CO)$_4$. Preferably, M is cobalt.

Illustrative, non-limiting examples of the compounds of this invention useful as hydroformylation catalyst, are:

(CH$_3$)$_2$N(CH$_2$)$_2$N(CH$_3$)$_2$CuCo(CO)$_4$;

[(C$_6$H$_5$)$_3$P]$_2$CuCo(CO)$_4$;

(CH$_3$)$_2$N(CH$_2$)$_2$N(CH$_3$)$_2$CuCo(CO)$_3$[(C$_6$H$_5$)$_3$P];

[(C$_6$H$_5$)$_3$P]$_2$CuCo(CO)$_3$[(C$_6$H$_5$)$_3$P];

(C$_6$H$_5$)$_2$PCH$_2$CH$_2$P(C$_6$H$_5$)$_2$CuCo(CO)$_4$;

(C$_6$H$_5$)$_2$P(CH$_2$)$_4$P(C$_6$H$_5$)$_2$CuCo(CO)$_4$; and (Ph$_3$P)$_3$CuCo(CO)$_3$(PBu$_3$).

The catalysts of this invention exhibit unexpected selectivity in that the predominent compounds formed in the hydroformylation of olefins are the preferred linear aldehydes. Of course, by selection of process conditions and the olefin, product yield can be shifted toward branched aldehydes or alcohols, if desired.

While the catalysts of this invention are primarily useful as hydroformylation catalyst they can be used for the hydrogenation of olefins. The olefins which can be converted to aldehydes utilizing the catalyst of this invention include C$_2$-C$_{20}$ aliphatic, cycloaliphatic and arylaliphatic olefinically unsaturated compounds or their substituted analogs where the substituents are hydroxyl or halogen. Illustrative, non-limiting examples of such olefins are ethylene, propylene, butene-1, butene-2; buta-1,3-diene; pent-1-ene, pent-2-ene, 2-methylbut-1-ene; penta-1,4-diene; isoprene, hex-1-ene, 4-methylpent-1-ene, 2-ethylbut-1-ene; 2,3 dimethylbut-1-ene; cyclohexene; 2,3 dimethylbuta-1,3-diene; hexa-1,5-diene; hept-1-ene, diisobutylene, myrcene, octene, octadec-1-ene, cyclopentene, cyclopentadiene, 2-vinylcyclohexene, terpene, pinene, camphene, octalin, dehydrodicyclopentadiene, styrene, methylstyrene, 1-phenylbuta-1,3-diene, vinylnaphthalene, vinylchloride, 1,2-dichloroethylene, allyl alcohol, butyl vinyl ether, allyl 2,4-dichlorophenyl ether; allylacetate, N-phthaloyl allyl amine, allyl trimethylsilane, etc.

The hydroformylation process of this invention is carried out at a pressure of about 5 MPa to about 20 MPa, and a temperature of about 130° C. to about 180° C. Preferably the reaction temperature is about 140° C. to about 160° C., e.g., 150° C. The reaction pressure is preferably about 6 MPa to about 16 MPa; more preferably about 8 MPa to about 12 MPa.

The advantages of the instant invention may be more readily appreciated by reference to the following examples:

EXAMPLE I

The method of preparation of the catalysts of this invention may be illustrated by the preparation of tmed-CuCo(CO)$_4$. Copper (I) iodide (1.01 g) was added to a solution of 0.62 g of tetramethylethylenediamine (tmed) in 100 ml of methylene chloride under a carbon monoxide atmosphere. The mixture was sirred for 15 minutes and 2.00 g of TlCo(CO)$_4$ was added. After an additional 15 minutes of stirring, the mixture was filtered to remove the TlI. The clear filtrate was evaporated under vacuum yielding 1.90 g of pale yellow tmedCuCo(CO)$_4$. The complex was purified by recrystallization from a methylene chloride-pentane mixture.

EXAMPLE II

The copper-cobalt carbonyl complexes of this invention were shown to be effective hydroformylation catalysts. In each of the hydroformylation reactions described below the vessel was a one-liter stirred Hastelloy autoclave (Autoclave Engineers). The catalyst complex was dissolved in a solvent and added to the autoclave. After sealing, the autoclave the olefin was added as a liquid from a separate pressure vessel. A mixture of 1:1 CO/H$_2$ was then added to the desired pressure. The vessel and contents were heated to the desired temperature with constant stirring. Additional CO and H$_2$ were added as needed until the reaction ceased. The vessel and contents were then cooled to room temperature, excess gases vented and the product recovered.

A. TMEDCuCo(CO)$_4$

To 350 ml of tetrahydrofuran (THF) was added 0.7 gm of catalyst. The mixture was introduced to the autoclave and 6.6 g of 2-butene were added. The CO/H$_2$ addition was to 6 MPa at room temperature. The reaction was carried out at 130° C. while the pressure was maintained at about 6 to 8 MPa by periodic addition of synthesis gas. The reactor contents weighed 368 g and comprised 15 g of isobutyralaldehyde and 23 g of n-butyralaldehyde.

B. TMEDCuCo(CO)$_4$

Run A was repeated except that after the addition of 5 MPa of 1:1 CO/H$_2$ at room temperature, 5 MPa of hydrogen was added. The reaction was carried out at 150° C. while the pressure was maintained at between 12 and 16 MPa by periodic addition of additional 1:1 synthesis gas.

The reactor contents weighed 365 gms and comprised 16 gms of isobutyraldehyde and 33 grams of n-butyraldehyde.

C. (Ph$_3$P)$_2$CuCo(CO)$_4$

To 300 ml of THF was added 1.4 gm of catalyst and the hydroformylation reaction was carried out in a manner similar to Run A using 64 gms of butene-1 as the olefin. The initial pressure of synthesis gas (1:1 CO/H$_2$) was 8 MPa. The reaction temperature was 150° C. and the reaction continued for 4 hrs. Reactor pressure was maintained between 10 and 15 MPa by periodic addition of synthesis gas.

The reactor contents weighed 313 grams and the product analysis showed that 16 grams of isobutyraldehyde and 41 grams of n-butyraldehyde were produced. This experiment demonstrates that the copper-cobalt-phosphine complexes of this invention are effective hydroformylation catalysts and have a high specificity for the more desirable linear product.

D. (Ph$_3$P)$_2$CuCo(CO)$_4$

Run C was repeated substituting 2-butene as the olefin (69 g). the reactor contents weighed 323 g. and analyzed 12 g. of isobutyraldehyde and 32 g. of n-butyraldehyde. This experiment demonstrates that the catalyst of this invention has specificity for the production of linear aldehydes even where the starting material for the hydroformylation process is an internal olefin such as 2-butene.

E. (Ph$_3$P)$_2$CuCo(CO)$_4$+Ph$_3$P

Run D was repeated except that 1.05 g. of triphenylphosphine was included in the reaction mixture. The reactor contents weighed 310 g. and analyzed 7 g. of isobutyraldehyde and 23 g. of n-butyraldehyde. This experiment demonstrates that the catalysts of this invention are effective hydroformylation catalysts with specificity for the production of normal aldehydes from internal olefins even in the presence of excess triphenylphosphine.

F. (Ph$_3$)$_2$CuCo(CO)$_4$

The Example of Run C was repeated with the exception that the solvent was 300 ml of methylisobutyl ketone and the olefin was 66 g. of 2-butene. All other process conditions were as in Run C.

The reactor contents weighed 325 g. and analysis showed that it contained 23 g. of isobutyraldehyde and 46 g. of n-butyraldehyde. This example demonstrates that selection of solvents is not critical when using the catalyst of this invention.

What is claimed is:

1. A hydroformylation catalyst having the structural formula:

$$T_aCuM(CO)_4$$

where L is a monodentate or bidentate phosphine, a is 1–3 and M is cobalt or rhodium.

2. The catalyst of claim 1 wherein the monodentate phosphine has the formula $$R_1R_2R_3P$$

where R$_1$, R$_2$ and R$_3$ are the same or different and are independently selected from the group consisting of alkyl, cycloalkyl, aryl, alkaryl and aralkyl.

3. The phosphine according to claim 2 wherein R$_1$, R$_2$ and R$_3$ are C$_1$–C$_8$ alkyl radicals.

4. The phosphine according to claim 3 wherein the C$_1$–C$_8$ alkyl radicals are selected from the group consisting of methyl, ethyl, propyl, butyl, pentyl, hexyl, heptyl and octyl.

5. The phosphine according to claim 2 wherein R$_1$, R$_2$ and R$_3$ are C$_5$–C$_8$ cycloalkyl radicals.

6. The phosphines according to claim 5 wherein the C$_5$–C$_8$ cycloalkyl radicals are cyclopentyl, cyclohexyl, methylcyclohexyl, cycloheptyl or cyclooctyl.

7. The phosphine according to claim 2 wherein R$_1$, R$_2$ and R$_3$ are independently selected from the group consisting of phenyl, benzyl, tolyl and xylyl.

8. The hydroformylation catalyst according to claim 1 wherein M is cobalt.

9. The hydroformylation catalyst according to claim 1 wherein M is rhodium.

10. The hydroformylation catalyst according to claim 1 of the formulae $(Ph_3P)_2CuCo(CO)_4$.

11. The catalyst according to claim 1 wherein the bidentate phosphine is a compound having the formula $[R_1R_2Q(CH_2)_nQR_3R_4]$
$R_1R_2P(CH_2)_nPR_3R_4$ wherein $R_1$, $R_2$, $R_3$ and $R_4$ are the same or different and are each independently selected from the group consisting of alkyl, cycloalkyl, aryl, alkaryl and aralkyl; and n is 1–4.

12. The catalyst according to claim 11 where $R_1$, $R_2$, $R_3$ and $R_4$ and $C_1$–$C_8$ alkyl, $C_5$–$C_8$ cycloalkyl aryl, $C_6$–$C_8$ aralyl or $C_6$–$C_8$ alkaryl.

13. The catalyst according to claim 12 wherein $R_1$, $R_2$, $R_3$ and $R_4$ are independently selected from the group consisting of methyl, ethyl, propyl, phenyl, benzyl and tolyl.

14. The catalyst according to claim 11 wherein $R_1$, $R_2$, $R_3$, and $R_4$, are each methyl.

15. The catalyst according to claim 11 wherein $R_1$, $R_2$, $R_3$, and $R_4$ are each phenyl.

16. The catalyst according to claim 1 wherein a is 1, M is cobalt and L is tetramethylethylene diamine.

17. The hydroformylation catalyst according to claim 11 wherein a is 1, M is cobalt and L is $(C_6H_5)_2PCH_2CH_2P(CH_6H_5)_2$.

18. The hydroformylation catalyst according to claim 11 wherein n=4, $R_1$, $R_2$, $R_3$ and $R_4$ are each phenyl and M is cobalt.

19. A hydroformylation catalyst having the formula tetramethylethylenediamine $CuCo(CO)_4$.

20. A hydroformylation catalyst having the formula $(R_1R_2N(CH_2)_nNR_3R_4)_aCuM(CO)_4$ wherein $R_1$, $R_2$, $R_3$ and $R_4$ are the same or different and are each independently selected from the group consisting of alkyl, cycloalkyl, aryl, alkaryl and aralkyl; n is 1–4; a is 1–3; and M is cobalt or rhodium.

21. The catalyst according to claim 20 where $R_1$, $R_2$, $R_3$ and $R_4$ are $C_1$–$C_8$ alkyl, $C_5$–$C_8$ cycloalkyl aryl, $C_6$–$C_8$ aralkyl or $C_6$–$C_8$ alkaryl.

22. The catalyst according to claim 21 wherein $R_1$, $R_2$, $R_3$ and $R_4$ are independently selected from the group consisting of methyl, ethyl, propyl, phenyl, benzyl and tolyl.

23. The hydroformylation catalyst according to claim 20 wherein M is cobalt.

24. The hydroformylation catalyst according to claim 20 wherein M is rhodium.

25. The catalyst according to claim 20 wherein $R_1$, $R_2$, $R_3$ and $R_4$ are each methyl.

26. The catalyst according to claim 20 wherein $R_1$, $R_2$, $R_3$ and $R_4$ are each phenyl.

27. The catalyst according to claim 20 wherein n is 2 and $R_1$, $R_2$, $R_3$ and $R_4$ are each methyl.

28. The hydroformylation catalyst according to claim 20 wherein n=4, $R_1$, $R_2$, $R_3$ and $R_4$ are each phenyl and M is cobalt.

* * * * *